United States Patent [19]
Tanaka et al.

[11] Patent Number: 5,728,544
[45] Date of Patent: *Mar. 17, 1998

[54] PROTEASE II

[75] Inventors: Yoshikazu Tanaka; Toshio Miyake; Satoshi Hanzawa; Seigou Oe; Shunichi Kidokoro, all of Kanagawa; Yoichiro Miki, Niigata; Kimiko Endo; Akiyoshi Wada, both of Tokyo, all of Japan

[73] Assignees: Sagami Chemical Research Center, Kanagawa, Japan; Holland Sweetner Company V.o.F., Maastricht, Netherlands

[*] Notice: The term of this patent shall not extend beyond the expiration date of Pat. No. 5,496,710.

[21] Appl. No.: 656,349
[22] PCT Filed: Dec. 6, 1994
[86] PCT No.: PCT/JP94/02050
§ 371 Date: Jun. 7, 1996
§ 102(e) Date: Jun. 7, 1996
[87] PCT Pub. No.: WO95/16029
PCT Pub. Date: Jun. 15, 1995

[30] Foreign Application Priority Data

Dec. 7, 1993 [JP] Japan .................. 5-306508

[51] Int. Cl.[6] .............. C12P 21/06; C12P 7/62; C12N 9/48; C12N 9/50; C12N 9/52; C12N 9/54; A61K 38/46
[52] U.S. Cl. .............. 435/68.1; 424/94.67; 435/135; 435/212; 435/219; 435/220; 435/221
[58] Field of Search ............. 424/94.67; 435/135, 435/68.1, 212, 219, 220, 221

[56] References Cited

U.S. PATENT DOCUMENTS 5,496,710  3/1996  Nagao et al. .............. 435/68.1

FOREIGN PATENT DOCUMENTS 2093199  12/1993  Canada .................. 435/68.1
616 033  9/1994  European Pat. Off. .

OTHER PUBLICATIONS

Kubo et al. (Jul. 1988) Cloning and Nucleotide Sequence of the Highly Thermostable Neutral Protease Gene from *Bacillus stearothermophilus*, J. General Microbiology 134: 1883–1892.

Imanaka et al: "A new way of enhancing the thermostability of proteases", Nature, vol. 324, No. 6098, Dec. 18, 1986, pp. 695–697.

Kubo et al: "Alteration of specific activity and stability of thermostable neutral protease by site directed mutagenesis", Appl Environ Microbiol, vol. 58, No. 11, 1992, pp. 3779–3783.

Kostrov et al: "Structure–finction relationship for *Bacilli* metalloproteases", oage 884; Biological Abstracts, vol. 87, No. 12, 1989, abstract No. 130218, & Mol. Biol., vol. 23, No. 1, 1989, pp. 255–265.

Database WPI, Section Ch, Week 9303, Derwent Publications Ltd., London, GB; AN 93–022706 & JP.A.04 349 883, Dec. 4, 1992.

*Primary Examiner*—Robert A. Wax
*Assistant Examiner*—Einar Stole
*Attorney, Agent, or Firm*—Cushman Darby & Cushman IP Group of Pillsbury Madison & Sutro, LLP

[57] ABSTRACT

A modified protease is disclosed, which is a mutant of the thermostable neutral metallo-protease having the amino acid sequence of SEQ ID NO:1 wherein the 150th aspartic acid residue is replaced with tryptophan.

6 Claims, 13 Drawing Sheets

SEQUENCE LISTING ( 1 ) GENERAL INFORMATION:

( i i i ) NUMBER OF SEQUENCES: 7

( 2 ) INFORMATION FOR SEQ ID NO: 1:

( i ) SEQUENCE CHARACTERISTICS:
        ( A ) LENGTH: 316 amino acids
        ( B ) TYPE: amino acid
        ( D ) TOPOLOGY: linear ( i i ) MOLECULE TYPE: protein ( x i ) SEQUENCE DESCRIPTION: SEQ ID NO: 1:

```
Ile Thr Gly Thr Ser Thr Val Gly Val Gly Arg Gly Val Leu Gly Asp
 1               5                  10                  15
Gln Lys Asn Ile Asn Thr Thr Tyr Ser Thr Tyr Tyr Tyr Leu Gln Asp
                20                  25                  30
Asn Thr Arg Gly Asn Gly Ile Phe Thr Tyr Asp Ala Lys Tyr Arg Thr
            35                  40                  45
Thr Leu Pro Gly Ser Leu Trp Ala Asp Ala Asp Asn Gln Phe Phe Ala
        50                  55                  60
Ser Tyr Asp Ala Pro Ala Val Asp Ala His Tyr Tyr Ala Gly Val Thr
65                  70                  75                  80
Tyr Asp Tyr Tyr Lys Asn Val His Asn Arg Leu Ser Tyr Asp Gly Asn
                85                  90                  95
Asn Ala Ala Ile Arg Ser Ser Val His Tyr Ser Gln Gly Tyr Asn Asn
            100                 105                 110
Ala Phe Trp Asn Gly Ser Gln Met Val Tyr Gly Asp Gly Asp Gly Gln
        115                 120                 125
Thr Phe Ile Pro Leu Ser Gly Gly Ile Asp Val Val Ala His Glu Leu
    130                 135                 140
Thr His Ala Val Thr Asp Tyr Thr Ala Gly Leu Ile Tyr Gln Asn Glu
145                 150                 155                 160
Ser Gly Ala Ile Asn Glu Ala Ile Ser Asp Ile Phe Gly Thr Leu Val
                165                 170                 175
Glu Phe Tyr Ala Asn Lys Asn Pro Asp Trp Glu Ile Gly Glu Asp Val
            180                 185                 190
Tyr Thr Pro Gly Ile Ser Gly Asp Ser Leu Arg Ser Met Ser Asp Pro
        195                 200                 205
Ala Lys Tyr Gly Asp Pro Asp His Tyr Ser Lys Arg Tyr Thr Gly Thr
    210                 215                 220
Gln Asp Asn Gly Gly Val His Ile Asn Ser Gly Ile Ile Asn Lys Ala
225                 230                 235                 240
Ala Tyr Leu Ile Ser Gln Gly Gly Thr His Tyr Gly Val Ser Val Val
                245                 250                 255
Gly Ile Gly Arg Asp Lys Leu Gly Lys Ile Phe Tyr Arg Ala Leu Thr
            260                 265                 270
Gln Tyr Leu Thr Pro Thr Ser Asn Phe Ser Gln Leu Arg Ala Ala Ala
        275                 280                 285
Val Gln Ser Ala Thr Asp Leu Tyr Gly Ser Thr Ser Gln Glu Val Ala
    290                 295                 300
Ser Val Lys Gln Ala Phe Asp Ala Val Gly Val Lys
305                 310                 315
```

( 2 ) INFORMATION FOR SEQ ID NO: 2:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 2:

AACGCATGCG GTAACCTGGT ATACAGC          27

( 2 ) INFORMATION FOR SEQ ID NO: 3:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 3:

GAGATACCAC TTTATTTCAC CCCT          24

( 2 ) INFORMATION FOR SEQ ID NO: 4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 4:

CGCAAGATCA TGGCGGGG          18

( 2 ) INFORMATION FOR SEQ ID NO: 5:

( i ) SEQUENCE CHARACTERISTICS:
        ( A ) LENGTH: 27 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 5:

TACCGCATGC GTTGACTCAT GTGCGAC          27

( 2 ) INFORMATION FOR SEQ ID NO: 6:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 6:

CCGAATTTGG ACACGAAAGG ATCC          24

( 2 ) INFORMATION FOR SEQ ID NO: 7:

( i ) SEQUENCE CHARACTERISTICS:
        ( A ) LENGTH: 27 base pairs
        ( B ) TYPE: nucleic acid ( C ) STRANDEDNESS: single
        ( D ) TOPOLOGY: linear ( i i ) MOLECULE TYPE: Other nucleic acid (synthetic DNA)

( x i ) SEQUENCE DESCRIPTION: SEQ ID NO: 7:

AACGCATGCG GTAACCNNNT ATACAGC                     27

PROTEASE II

This application claims benefit of International application PCT/JP94/02050, filed Dec. 6, 1994.

FIELD OF THE INVENTION

This invention relates to novel thermolysin-like neutral metallo-proteases and to use thereof, more specifically in the production of benzyloxycarbonyl-α-L-aspartyl-L-phenylalanine methyl ester.

Thermolysin is a useful enzyme which is commercially available and used in a wide variety of fields, for example in detergent compositions, in food processing and in cosmetic formulations. It is further used in the synthesis of benzyloxycarbonyl-α-L-aspartyl-L-phenylalanine methyl ester (hereinafter referred to briefly as Z-APM), which is a precursor of aspartame, an artificial sweetener.

BACKGROUND OF THE INVENTION

Thermolysin was first found in the culture broth of *Bacillus thermoproteolyticus* (Endo, s. (1962) J. Fermentation Tech., 40, 346–353) and a number of investigations have been conducted thereon. Thus, for instance, its amino acid sequence (Titani, K., et al., (1972) Nature New Biol., 238, 35–37) and the three-dimensional structure of the enzyme (Holmes, M. A. and Matthews, B. W., (1982) J. Mol. Biol. 160., 623–639) have been elucidated. Meanwhile, the protease gene was cloned from *Bacillus thermoproteolyticus* (EP-A-0418625) and the amino acid sequence of the mature enzyme as deduced from the nucleotide sequence of said gene was found to be different from the original primary structure as shown by Titani in two positions. Thus, it was reported that the 37th (from the amino terminal) amino acid residue of the mature enzyme is not aspartic acid but asparagine and the 119th one is not glutamic acid but glutamine. This amino acid sequence is identical with that coded by nprM, one of the protease genes cloned from *Bacillus thermoproteolyticus* (Kubo, M., et al., (1988) Journal of General Microbiology 134, 1883–1892).

Therefore, in the present specification, the protease coded by this nprM gene or the gene from *Bacillus thermoproteolyticus* is referred to as "wild type thermolysin-like neutral metallo-protease".

Alteration of specific activity and stability of thermolysin-like neutral metallo-protease has been reported (Kubo M., et al., (1992) Applied and Environmental Microbiology, 58, 3779–3783). In this article various mutants have been described which differ in one or more amino acid residues in the primary structure, especially at positions 93, 110, 114, 115, 136, 137, 143, 151, 157, 193, 211, 217 and 221. But in this reference, the activity was measured only by casein digestion method. None of these mutants, however, did show any substantially improved activity in relation to Z-APM synthesis or digestion. It now (as described further in the examples of previous European patent application of the applicant, application No. 93200773.5) also has been established that the activity for casein digestion does not correlate to that for Z-APM synthesis: it appears that even if the specific activity for casein digestion increases, the specific activity for Z-APM synthesis does not always increase.

In addition, the applicant previously found that useful novel proteases could be derived from thermolysin-like neutral metallo-protease having the (wild type) amino acid sequence of SEQ ID NO:1 shown below, by replacing one or more amino acid residues at certain positions with other amino acid residues than original ones.

(SEQ ID NO:1)

Ile Thr Gly Thr Ser Thr Val Gly Val Gly Arg Gly Val Leu Gly
1               5                   10                  15
Asp Gln Lys Asn Ile Asn Thr Thr Tyr Ser Thr Tyr Tyr Tyr Leu
                20                  25                  30
Gln Asp Asn Thr Arg Gly Asn Gly Ile Phe Thr Tyr Asp Ala Lys
                35                  40                  45
Tyr Arg Thr Thr Leu Pro Gly Ser Leu Trp Ala Asp Ala Asp Asn
                50                  55                  60
Gln Phe Phe Ala Ser Tyr Asp Ala Pro Ala Val Asp Ala His Tyr
                65                  70                  75
Tyr Ala Gly Val Thr Tyr Asp Tyr Tyr Lys Asn Val His Asn Arg
                80                  85                  90
Leu Ser Tyr Asp Gly Asn Asn Ala Ala Ile Arg Ser Ser Val His
                95                  100                 105
Tyr Ser Gln Gly Tyr Asn Asn Ala Phe Trp Asn Gly Ser Gln Met
                110                 115                 120
Val Tyr Gly Asp Gly Asp Gly Gln Thr Phe Ile Pro Leu Ser Gly
                125                 130                 135
Gly Ile Asp Val Val Ala His Glu Leu Thr His Ala Val Thr Asp
                140                 145                 150
Tyr Thr Ala Gly Leu Ile Tyr Gln Asn Glu Ser Gly Ala Ile Asn
                155                 160                 165
Glu Ala Ile Ser Asp Ile Phe Gly Thr Leu Val Glu Phe Tyr Ala
                170                 175                 180
Asn Lys Asn Pro Asp Trp Glu Ile Gly Glu Asp Val Tyr Thr Pro
                185                 190                 195
Gly Ile Ser Gly Asp Ser Leu Arg Ser Met Ser Asp Pro Ala Lys
                200                 205                 210
Tyr Gly Asp Pro Asp His Tyr Ser Lys Arg Tyr Thr Gly Thr Gln
                215                 220                 225
Asp Asn Gly Gly Val His Ile Asn Ser Gly Ile Ile Asn Lys Ala
                230                 235                 240
Ala Tyr Leu Ile Ser Gln Gly Gly Thr His Tyr Gly Val Ser Val
                245                 250                 255
Val Gly Ile Gly Arg Asp Lys Leu Gly Lys Ile Phe Tyr Asg Ala
                260                 265                 270
Leu Thr Gln Tyr Leu Thr Pro Thr Ser Asn Phe Ser Gln Leu Arg
                275                 280                 285
Ala Ala Ala Val Gln Ser Ala Thr Asp Leu Tyr Gly Ser Thr Ser
                290                 295                 300
Gln Glu Val Ala Ser Val Lys Gln Ala Phe Asp Ala Val Gly Val
                305                 310                 315
Lys

Specifically, applicant already filed a European patent application (Application No. 93200773.5) for such novel modified proteases obtained from said wild type by replacement of at least one of the following amino acid residues with an amino acid different therefrom: 144th (leucine), 150th (aspartic acid), 187th (glutamic acid) and 227th (asparagine) amino acid residues.

The specific activity of the modified enzymes mentioned in said earlier patent application (not yet laid open at the date of filing of the present application) and having the single amino acid replacement at one of the positions 144th, 150th, 187th and 227th was not larger than 2 times of that of the wild type enzyme for synthesis or digestion of Z-APM.

Based on these observations, and because there are various problems in the enzymatic synthesis of Z-APM, such as relatively low activity of the enzyme, inactivation of the enzyme during the condensation reaction and hydrolysis of the product Z-APM and the starting material and L- or D,L-phenylalanine methyl ester (PM), due to the long reaction time, and/or unfavorable pH conditions, there is still need to develop improved enzymes that have higher activity for the synthesis of Z-APM. Of course where PM is mentioned in this application also its salts can be included in the meaning of the term PM.

SUMMARY OF THE INVENTION

Now surprisingly, it has been found that the activity enhancement of modified enzyme having a tryptophan residue at the 150th position in SEQ ID NO:1 is even extremely larger than those of previously described modified proteases.

From these observations, the present invention was completed and hereby provides the modified proteases having the amino acid sequence as shown above (SEQ ID NO:1), but with replacement(s) of at least the 150th amino acid residue from aspartic acid (wild type) to tryptophan. It thus provides an improved enhancement of the activity of Z-APM synthesis of the thermolysin-like neutral metalloprotease derived from *Bacillus stearothermophilus*.

The modified proteases according to the present invention therefore are very useful in the production of Z-APM at large scale.

DETAILED DESCRIPTION OF THE INVENTION

Figure 1:
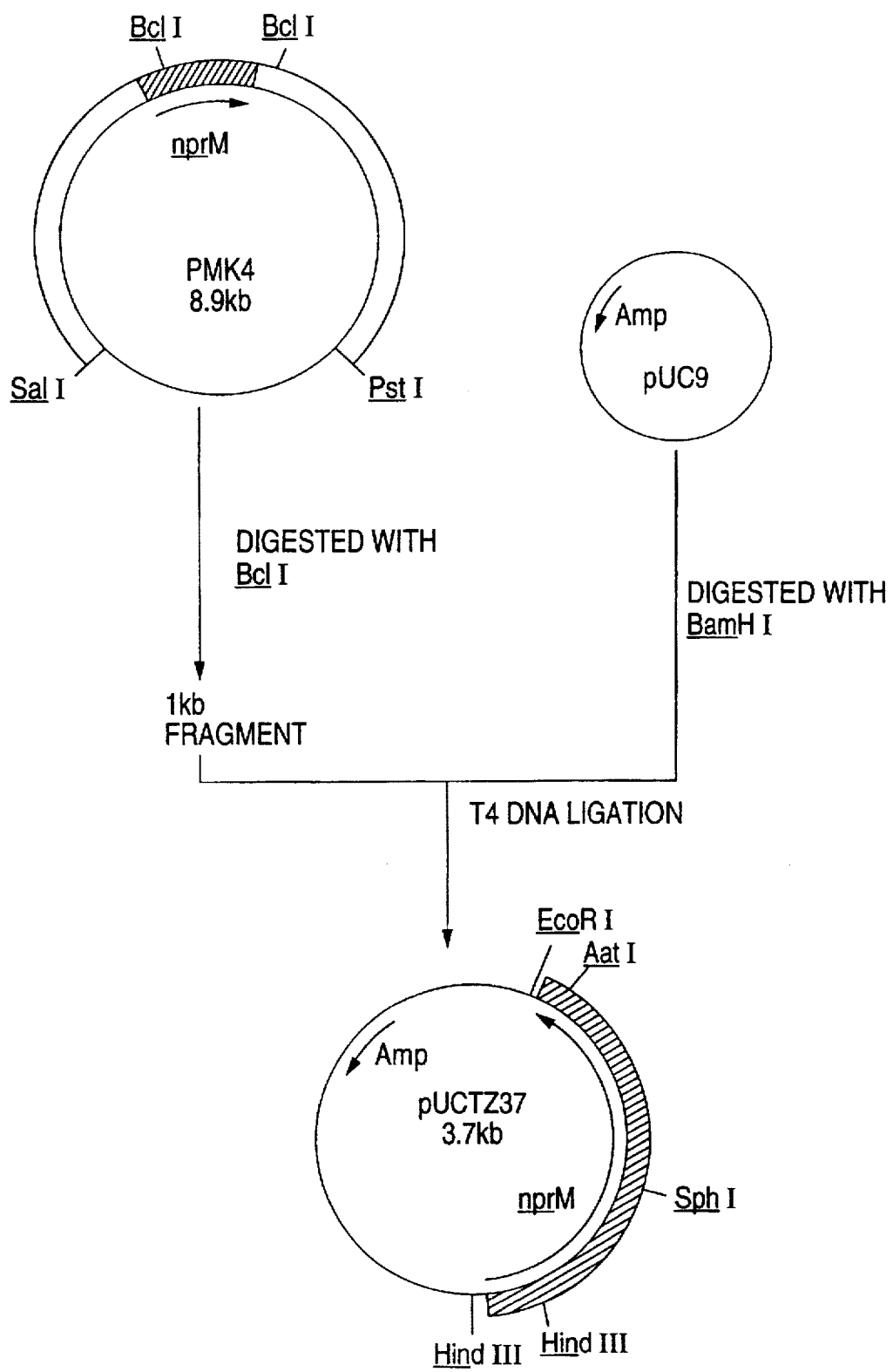
FIG. 1 shows the scheme used for constructing a recombinant plasmid named pUCTZ37 from the known plasmid pMK4.

In the above mentioned earlier patent application modified proteases which had the replacement at the 150th position from aspartic acid to asparagine, histidine and lysine were disclosed. The activities of these modified proteases for Z-APM synthesis or hydrolysis were at best 2 times higher than that of wild type thermolysin-like neutral metallo-protease.

The novel modified proteases according to the present invention are derivatives having a tryptophan residue instead of the aspartic acid residue at the 150th position of thermolysin-like neutral metallo-protease of SEQ ID NO:1 (They are also designated hereinafter as D150W). In particular these novel proteases have a highly enhanced activity for Z-APM synthesis and/or digestion. The suitability of the proteases obtained can be determined by assay tests for the ultimate applications. Typically, this is determined by analyzing the activity for Z-APM synthesis and/or digestion, and comparing these activities with that of wild type thermolysin-like neutral metallo-protease assayed in the same manner. This procedure is described further in the examples.

Other positions of the modified protease (D150W) can be replaced with other amino acid residues. For example, a two-site mutant which is replaced at the 150th position from aspartic acid to tryptophan and at the 227th position from asparagine to histidine (D150W-N227H) and a three-site mutant which is replaced at the 144th residue from leucine to serine, the 150th position from aspartic acid to tryptophan and the 227th position from asparagine to histidine (L144S-D150W-N227H) were synthesized and shown to be very active and stable in Z-APM synthesis.

Modified enzymes can be produced by methods known per se to those skilled in the art.

Various methods are known which can be used to introduce mutations into cloned DNAs. For example, mutant nprM gene fragments can be prepared by using the M13 phage mutagenesis method (Vandeyar, M., et al., (1988) Gene, 65, 129).

The plasmid and phage DNAs used for templates in this method, can be derived from the known plasmid pMK1 (Kubo, M. and Imanaka, T., (1989) J. Bacteriol, 171, 4080–4082). Several restriction endonucleases can be used for digestion and cloning of the fragments of nprM gene into another plasmid or into phage vectors. The mutagenic primers should be complementary to the single-stranded template DNA containing the nprM gene, except for the codon(s) for the replaced amino acid residue(s). Various nucleotide sequences are conceivable for that purpose. By using these mutagenic primers which have (a) different codon(s) for the replaced amino acid residue(s), any desired amino acid replacement can be attained.

Alternatively, the nprM gene can be mutated by the PCR technique (polymerase chain reaction) using chemically synthesized primers (Higuchi, R., Krummel, B., and Saiki, R. K., (1988) Nucleic Acids Res. 16, 7351–7367). When a restriction enzyme site exists in the vicinity of the site of mutation, this PCR method is particularly useful. Since, for example, there is a cleavage site for the restriction enzyme SphI in the vicinity of the codon for aspartic acid in the 150th position of the wild type thermolysin-like metallo-protease, mutagenic primers containing this SphI site can be used for producing mutants in the 150th position. The mutagenic primer thus is used as a sense primer. As the reverse-direction primer (antisense), an oligonucleotide can be used, which is complementary to the nprM gene downstream from, for example, the AatI cleavage site of the nprM gene.

Two methods can be used for effecting mutagenesis at more than one site. One method comprises effecting simultaneous mutagenesis at all the target sites, while the other comprises introduction of mutations one after the other. Both methods actually give plasmids with mutations at more than one site.

A general method for recombinant thermolysin-like neutral metallo-protease preparation is described in the literature (Kubo, M. and Imanaka, T., (1989) J. Bacteriol., 171, 4080–4082) and comprises: insertion of the DNA encoding the modified thermolysin-like neutral metallo-protease into an expression vector, using this vector to transform a host cell, culturing the transformant until the modified metallo-protease accumulates in the culture and then recovering modified enzyme from the culture. However, the plasmid pMK1 used in this reference is more than 20 kb in size and therefore it is substantially difficult to transform *Escherichia coli* with said plasmid. Furthermore, it was found that, in *Bacillus subtilis* too, the plasmid pMK1 drops out to a considerable extent in the latter stage of cultivation.

Therefore, to overcome such problems the inventors constructed shuttle vectors with which both hosts, *Escherichia coli* and *Bacillus subtilis* can be transformed and which can express the nprM gene in these hosts. As shown in FIG. 1 to FIG. 4, two shuttle vectors containing the nprM gene have been thus constructed (pUBTZ1 and pUBTZ2). When these are used to transform such strains of *Escherichia coli* as HB101 and JM103, the nprM gene is expressed in those strains. In addition, transformation of such *Bacillus subtilis* strains as DB104, DB117 and MT-2 with these plasmids led to successful expression of the nprM gene. Also no drop-out is observed in the latter stage of cultivation.

Similar results and advantages of using these shuttle vectors are obtained by using the modified thermolysin-like neutral metallo-protease genes instead of the wild type gene.

The modified thermolysin-like neutral metallo-protease can be produced in recombinant bacteria and is secreted in culture media. These proteases can be recovered by ammonium sulfate precipitation and purified to homogeneity in the conventional manner, for example by hydrophobic interaction chromatography and/or gel filtration.

The modified proteases can be used to synthesize Z-APM, which is a precursor of aspartame, more effectively than wild type thermolysin-like neutral metallo-protease. This is indicated by comparing the activities for the Z-APM digestion and Z-APM synthesis of these modified proteases to those of the wild-type enzyme. These are to be found extremely higher than those of the wild type enzyme and of the modified proteases described in the above mentioned European patent application (application No. 93200773.5). The measured values of these activities will be described in the following examples.

As stated above the novel modified proteases according to the present invention are proteases of thermolysin-like neutral metallo-protease of SEQ ID NO:1 wherein the 150th aspartic acid residue is replaced with tryptophan(D150W).

It is to be noted that the activity of casein digestion is not related to the activity of Z-APM synthesis or digestion. When the activities of mutant enzymes for casein and Z-APM are compared, it is clear that even if the activity for casein digestion is decreased, the activity for Z-APM synthesis and/or digestion can greatly be enhanced. The following examples are given only for illustrating the present invention and are by no means limitative of the scope of the invention.

EXAMPLE 1

[Synthesis of the Modified Protease which has the Replacement at the 150th Amino Acid Residue from Aspartic Acid to Tryptophan (D150W)]

a) Construction of the expression plasmid pUBTZ2 containing wild type nprM gene.

From a plasmid pMK4 (Yamada et al., (1991) Gene, 99, 109–114), the about 1.0 kb DNA fragment containing part of the nprM gene which was obtained by digestion with BclI was cloned in BamHI site of a plasmid pUC9 to construct a plasmid pUCTZ37 (FIG. 1).

Figure 2:
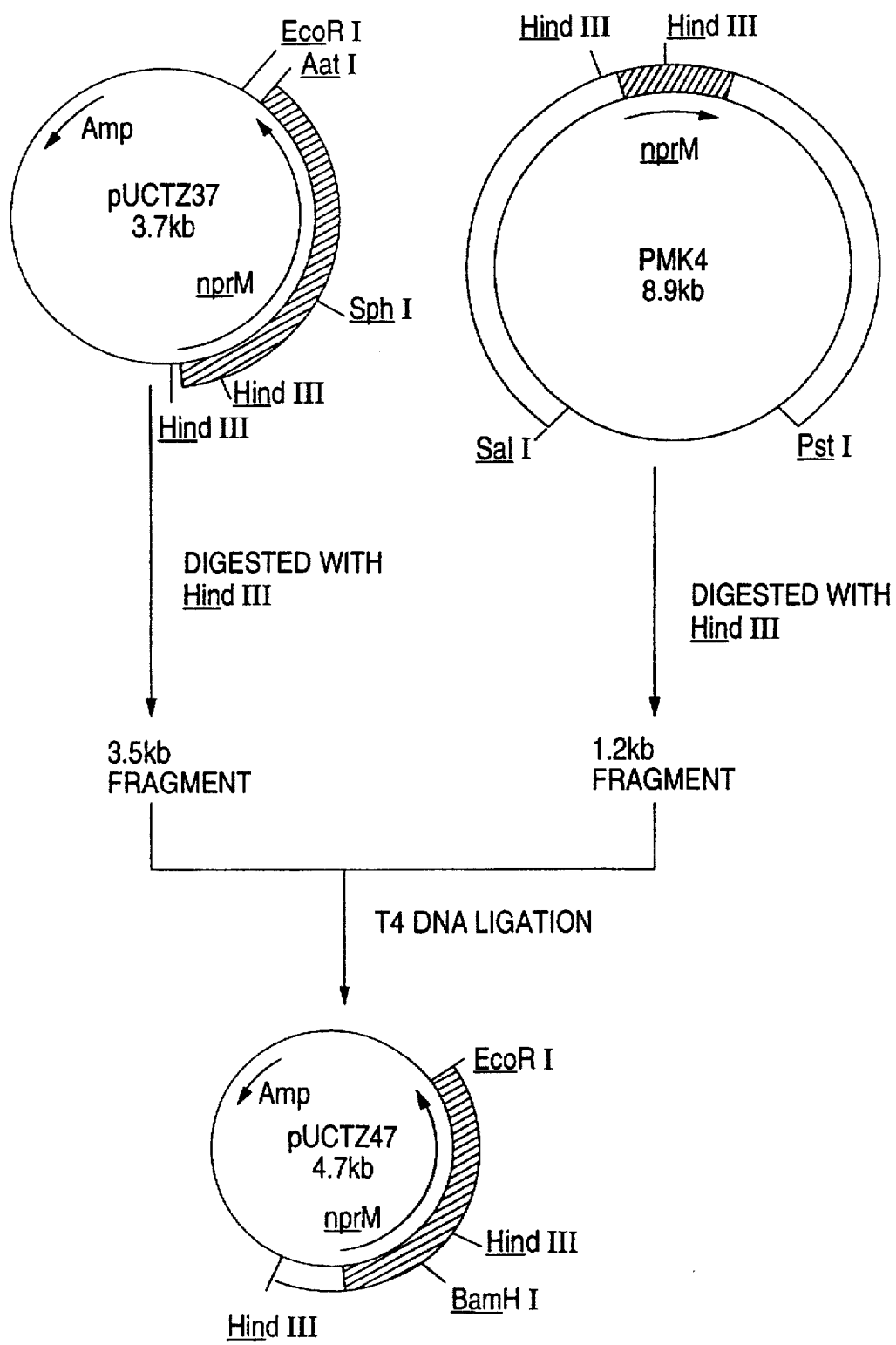
FIG. 2 shows the scheme used for constructing a recombinant plasmid named pUCTZ47 from the plasmid pMK4 and the plasmid pUCTZ37.

The plasmid pUCTZ37 was an incomplete one not having the 5'-terminal region of nprM gene. The plasmid pUCTZ37 was digested with restriction endonuclease HindIII and the about 1.2 kb HindIII fragment of pMK4 was cloned into the larger pUCTZ37 fragment to construct plasmid pUCTZ47 (FIG. 2). The recombinant plasmid pUCTZ47 contains the full length sequence of nprM and its transcriptional promotor sequence.

Figure 3:
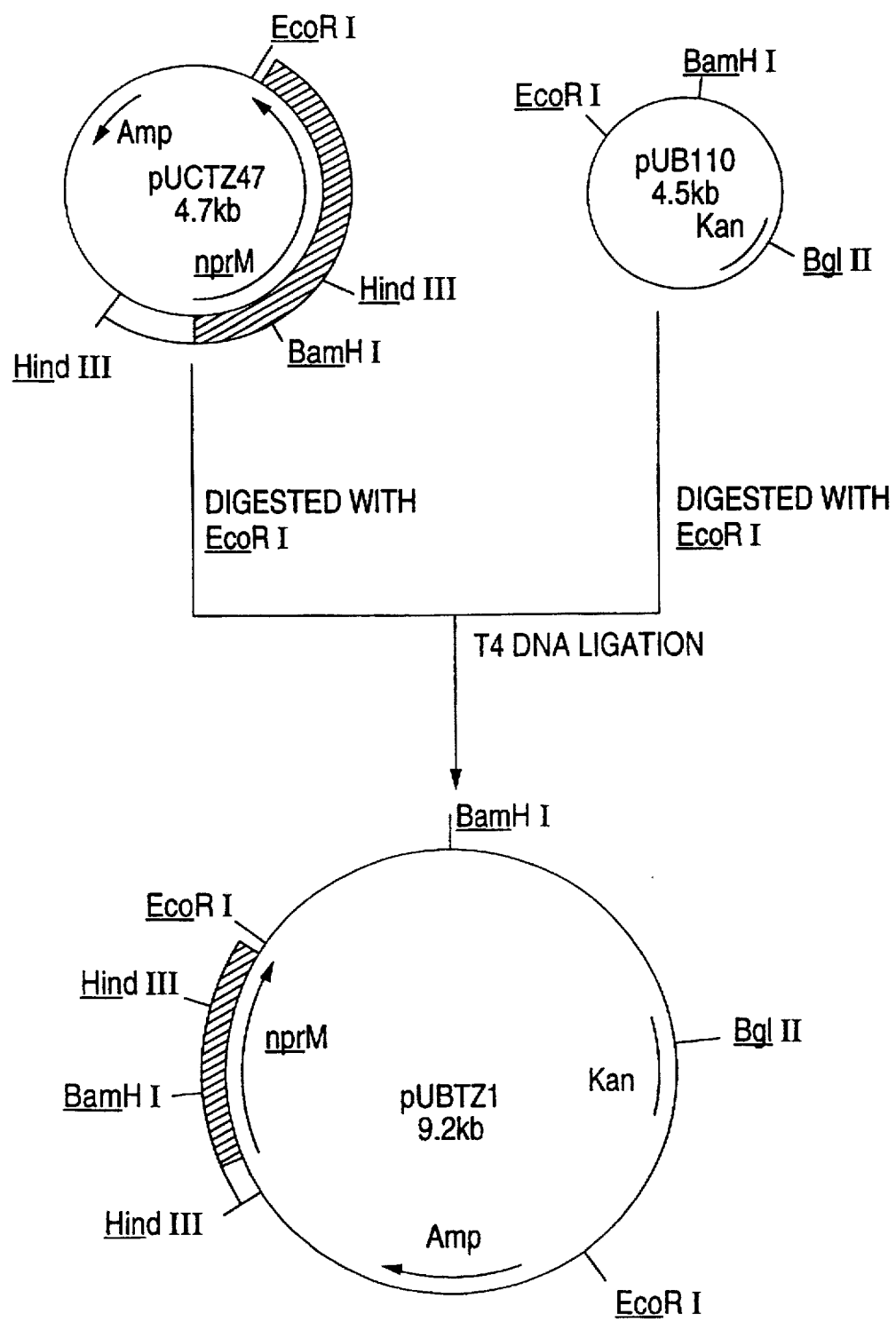
FIG. 3 shows the scheme used for constructing a recombinant plasmid named pUBTZ1 from the known plasmid pUCTZ47 and the plasmid pUB110.

To construct shuttle vectors between *Escherichia coli* and *Bacillus subtilis*, both pUCTZ47 and pUB110 (Keggins, K. M. et al, Proc. Natl. Ac. Sci. USA, (1978), 75, 1423–1427) were digested with EcoRI and ligated with T4 DNA ligase to construct plasmid pUBTZ1, as shown in FIG. 3.

Figure 4:
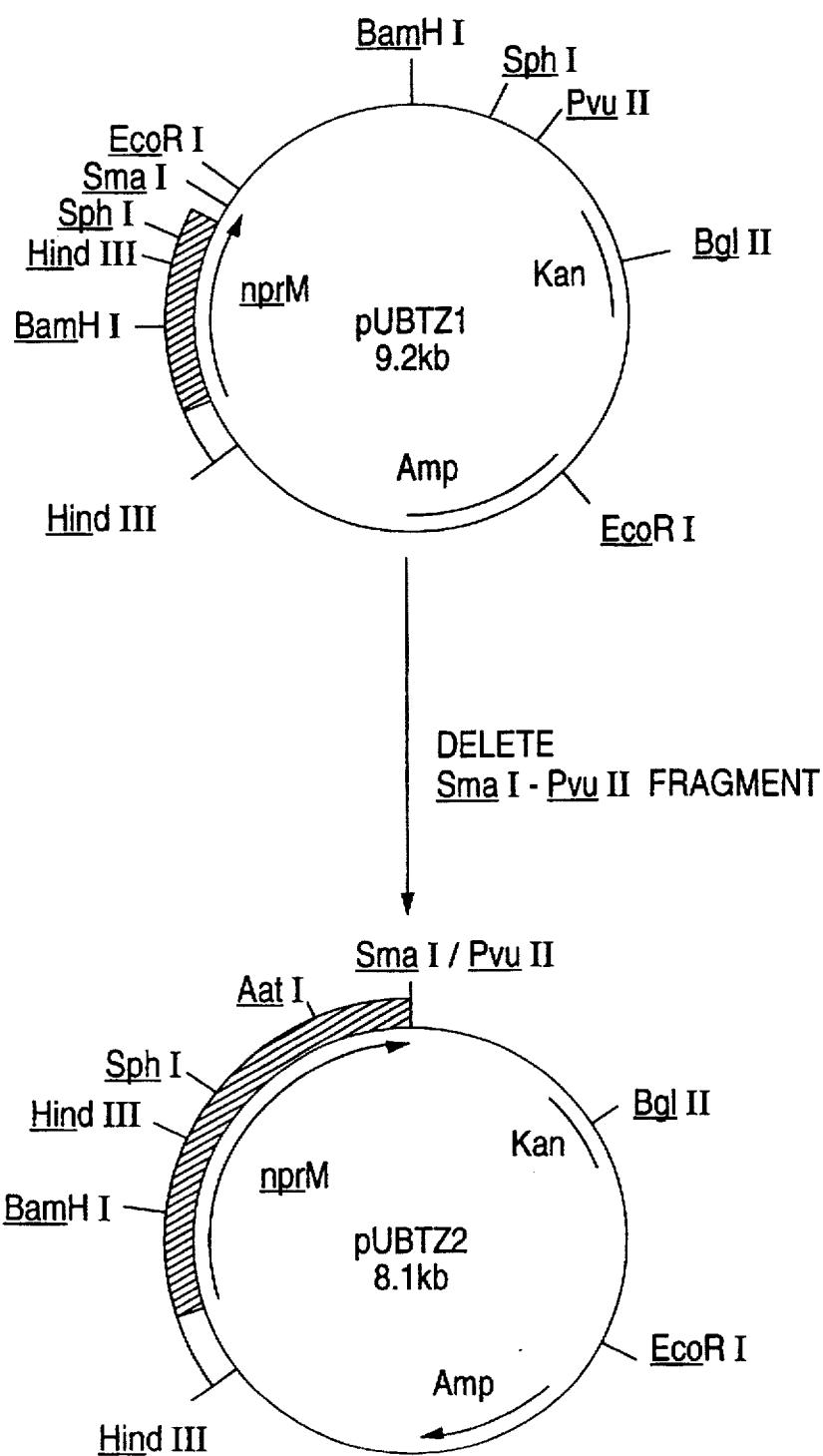
FIG. 4 shows the scheme used for constructing a recombinant plasmid named pUBTZ2 from the plasmid pUBTZ1.

Finally, the DNA fragment between the SmaI and PvuII restriction sites was deleted from the plasmid pUBTZ1 as shown in FIG. 4, to construct plasmid pUBTZ2.

Plasmid pUBTZ2 has single BamHI, SphI and AatI restriction sites in the nprM gene.

b) Site 150 Trp mutagenesis

The oligonucleotides used for the mutagenesis were synthesised by using a DNA synthesizer Model 380B produced by Applied Biosystems Co. LTD. The nucleotide sequence of the mutagenesis primer was (SEQ ID NO:2)
5'-AACGCATGCGGTAACCTGGTATACAGC-3'
      SphI          Trp
                      150

Furthermore, a reverse-direction primer was synthesized having the nucleotide sequence described below.
(SEQ ID NO:3)

5' - GAGATACCACTTTATTTCACCCCT - 3'

1 ng of plasmid pUBTZ2 was dissolved in 100 µl of the reaction mixture for PCR (67 mM Tris-hydrochloride (pH 8.8), 16.6 mM ammonium sulfate, 6.7 mM MgCl2, 10 mM 2-mercaptoethanol, 0.05 mM dATP, 0.05 mM dTTP, 0.05 mM dGTP, 0.05 mM dCTP, 1 µM mutagenesis primer, 1 µM reverse-direction primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA.

20 μl of a reaction mixture (50 mM Tris-hydrochloride at pH 7.5, 10 mM MgCl2, 0.1M NaCl, 1 mM DTT) containing half the amount of the amplified DNA was digested with 5 units each of restriction enzyme SphI and AatI at 37° C. for 2 hours, and was incubated at 70° C. for 5 minutes. The mutated SphI-AatI fragment was ligated with the SphI-AatI fragment of pUBTZ2 (7.6 kb) using a Takara Shuzo DNA ligation kit. The ligation mixture was used to transform *Escherichia coli* JM103 in a conventional method to give a transformant JM103/pUBTZ2 (D150W). The substituted amino acid was confirmed by the determination of the nucleotide sequence of this plasmid.

c) Preparation of purified mutant enzyme from recombinant *Bacillus subtilis*

The plasmid DNA above was extracted by the rapid alkaline-SDS method (Maniatis, T., Fritsch E. F., Sambrook, Jr., (1989) Molecular Cloning: a laboratory manual (2nd Ed.) Cold Spring Harbor Laboratory Press, Cold Spring Harbor, N.Y. USA. 1.25–1.28). Transformation to *Bacillus subtilis* MT-2 strain was done by the competent cell method (Hardy, K. G., (1985) in: Glover, D. M., ed., DNA Cloning Volume II (1st ed), IRL Press Limited, Oxford, England, 1–17).

A single colony of the thus obtained transformant *Bacillus subtilis* MT-2/pUBTZ2(D150W) was transferred to 5 ml of LB medium containing kanamycin (5 μg/ml) and incubated at 37° C. overnight. The culture was transferred to 500 ml of 2 L medium (2% Bacto tryptone, 1% yeast extract, 0.5% NaCl) containing kanamycin (5 μg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of Buffer A (20 mM Tris-hydrochloride at pH 9.0, 10 mM CaCl2). The solution was applied to 20 ml of Butyl-Toyopearl, followed by elution with Buffer A at a flow rate of 1.5 ml/minute. Active fractions were combined and subjected to salting out with 60% saturated ammonium sulfate. The precipitate was collected by centrifugation at 15,000 rpm for 30 minutes, and dissolved in 5 ml of Buffer B (10 mM Tris-hydrochloride at pH 7.0, 0.1M NaCl, 10 mM CaCl2). The enzyme solution was further applied to a gel-filtration column (TSK Gel G2000 (SW 21.5×300 mm)), followed by elution with Buffer B at a flow rate of 1 ml/minute. Active fractions were combined to give purified enzyme.

Figure 5:
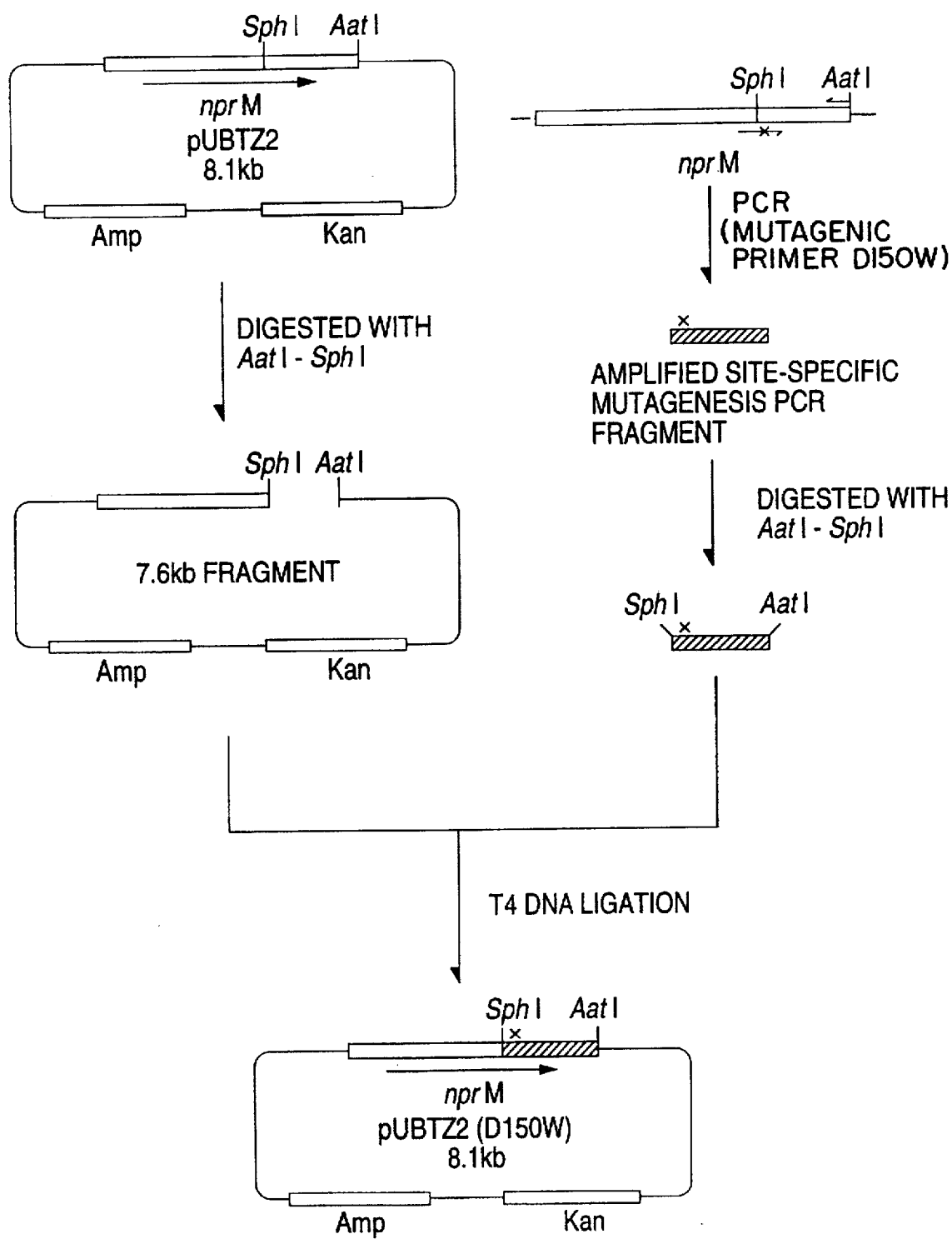
FIG. 5 shows the scheme used for constructing a recombinant plasmid named pUBTZ2(D150W) from the plasmid pUBTZ2 and the mutant DNA fragment obtained by polymerase chain reaction.

FIG. 5 shows the scheme used for constructing recombinant plasmid pUBTZ2 (D150W).

EXAMPLE 2

[Synthesis of the Modified Protease which has the Double Replacements at the 150th Amino Acid Residue from Aspartic Acid to Tryptophan and the 227th Amino Acid Residue from Asparagine to Histidine (D150W-N227H)]

The D150W-N227H two-site mutant of thermolysin-like neutral metalloprotease was constructed as follows.

a) Site 227 His mutagenesis

1 μg of the plasmid pMK1 containing the thermolysin-like neutral metallo-protease gene nprM derived from *Bacillus stearothermophilus* MK 232 (Kubo, M. and Imanaka, T., (1989) J. Bacteriol 171, 4080–4082) was digested with 5 units of each of restriction enzyme PstI and BamHI in 20 μl of a reaction mixture (50 mM Tris-hydrochloride at pH 7.5, 10 mM MgCl2, 0.1M NaCl, 1 mM DTT) at 37° C. for 2 hours. The sample was subjected to 1% agarose gel electrophoresis, and an approximately 3.5 kb DNA fragment was separated and purified using a Bio-101 Gene Clean DNA purification kit.

Separately, 1 μg of the plasmid pUC9 was digested with 5 units of each of restriction enzyme PstI and BamHI in 20 μl of the same reaction mixture as mentioned above at 37° C. for 2 hours.

Figure 6:
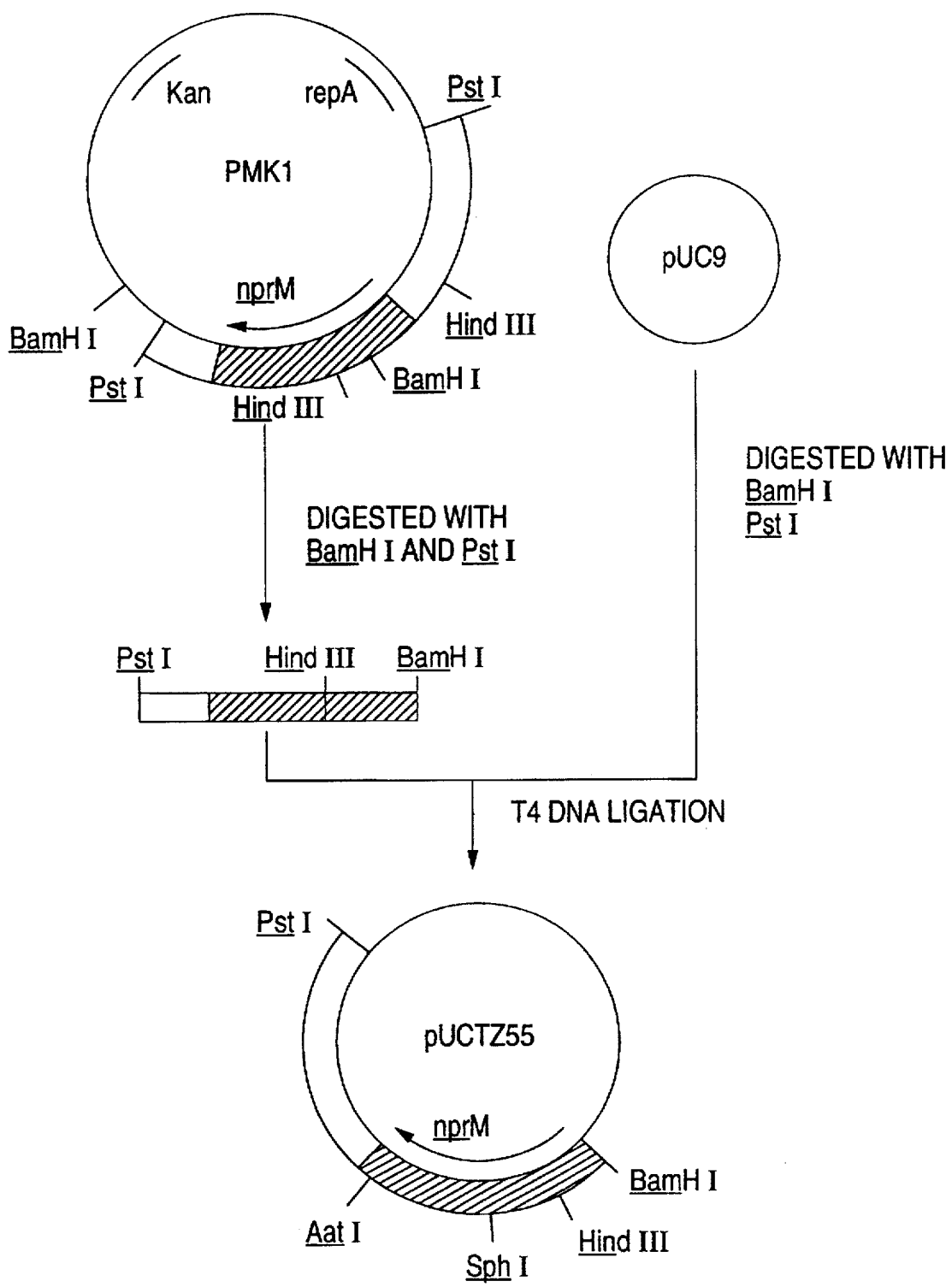
FIG. 6 shows the scheme used for constructing a recombinant plasmid named pUCTZ55 from the known plasmid pMK1.

The PstI-BamHI fragment of the nprM gene was ligated with the PstI-BamHI fragment of pUC9 using a Takara Shuzo DNA ligation kit. The ligation mixture was used to transform *Escherichia coli* JM109 in a conventional method to give a recombinant plasmid (pUCTZ55) containing the PstI-BamHI fragment of the nprM gene (FIG. 6).

1 μg of the recombinant plasmid pUCTZ55 was digested with 5 units of each of SphI and BclI in 20 μl of a reaction mixture (50 mM Tris-hydrochloride at pH 7.5, 10 mM MgCl2, 0.1M NaCl, 1 mM DTT) at 37° C. for 2 hours. The sample was subjected to 1% agarose gel electrophoresis and an approximately 550 bp DNA fragment was separated and purified using a Bio-101 Gene Clean DNA purification kit.

Separately, 1 μg of the phage vector M13mp18 was digested with 5 units of each of restriction enzyme SphI and BamHI in 20 μl of the same reaction mixture as mentioned above at 37° C. for 2 hours.

Figure 7:
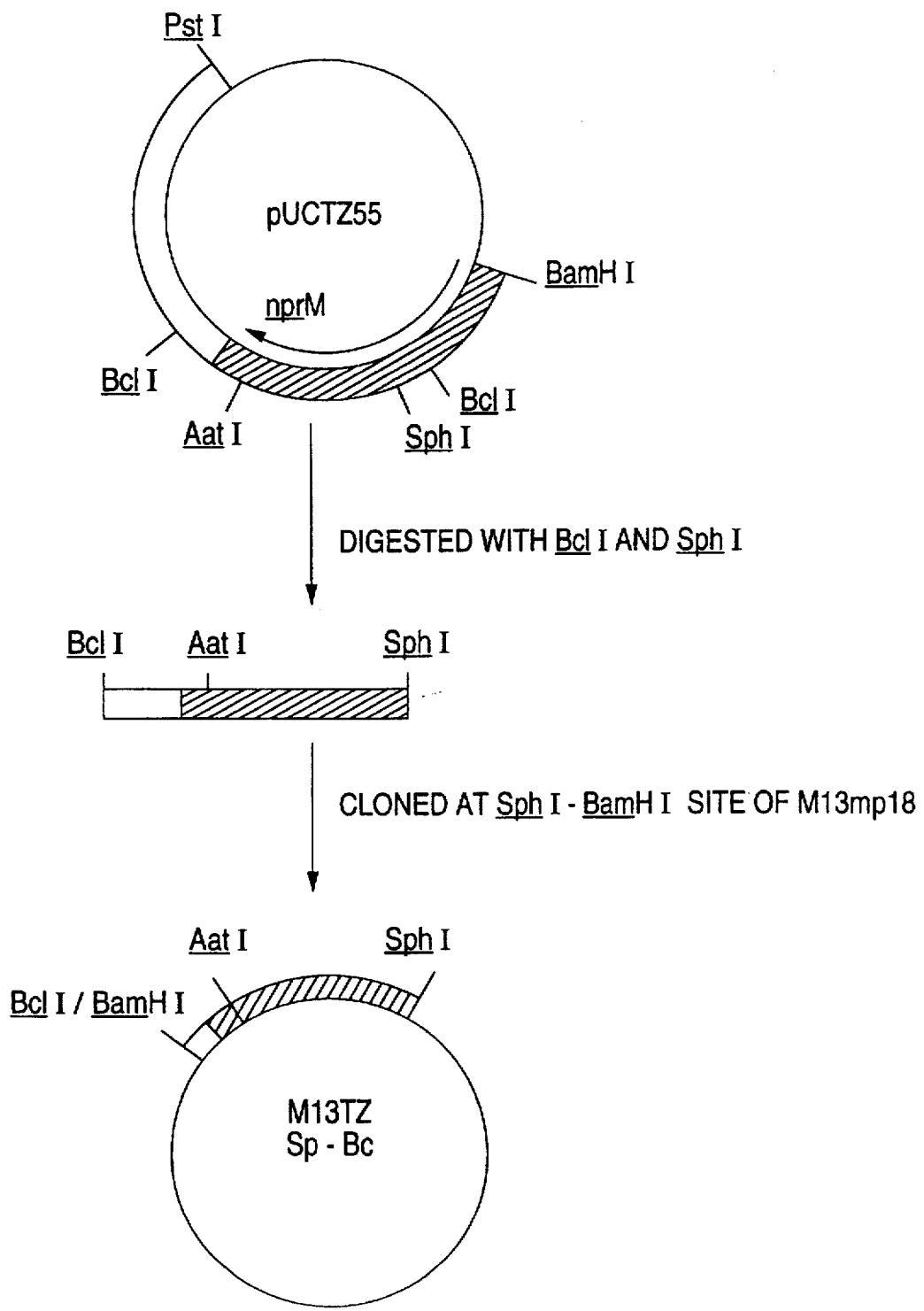
FIG. 7 shows the scheme used for constructing a recombinant M13 phage named M13TZSp-Bc from the plasmid pUCTZ55.

The SphI-BclI fragment of the nprM gene was ligated with the SphI-BamHI fragment of M13mp18 using a Takara Shuzo DNA ligation kit. The ligation mixture was used to transform *Escherichia coli* JM109 in a conventional method to give a recombinant phage (M13TZSp-Bc) containing the SphI-BclI fragment of the nprM gene (FIG. 7).

The single stranded DNA was prepared from the M13TZSp-Bc by a conventional method and subjected to mutagenesis. The oligonucleotides used for mutagenesis were prepared using an Applied Biosystems model 380B DNA synthesizer.

The mutagenic oligonucleotide used for the replacement of the 227th residue (asparagine to histidine) is shown below.

(SEQ ID NO:4)
5'-CGCAAGATCATGGCGGGG-3'
His
227

The mutagenesis was performed using a USB T7-GEN in vitro mutagenesis kit, followed by DNA sequencing for confirmation of the mutation.

The double-stranded DNA of the mutated M13TZSp-Bc was prepared by a conventional method and 1 μg of the double-stranded DNA was digested with 5 units of each of restriction enzyme SphI and AatI in 20 μl of a reaction mixture (50 mM Tris-hydrochloride at pH 7.5, 10 mM MgCl2, 0.1M NaCl, 1 mM DTT) at 37° C. for 2 hours, and was electrophoresed on a 1% agarose gel. A DNA fragment of about 550 bp was isolated from the M13TZSp-Bc digests and the DNA fragment was purified using a Bio-101 Gene Clean DNA purification kit.

Figure 8:
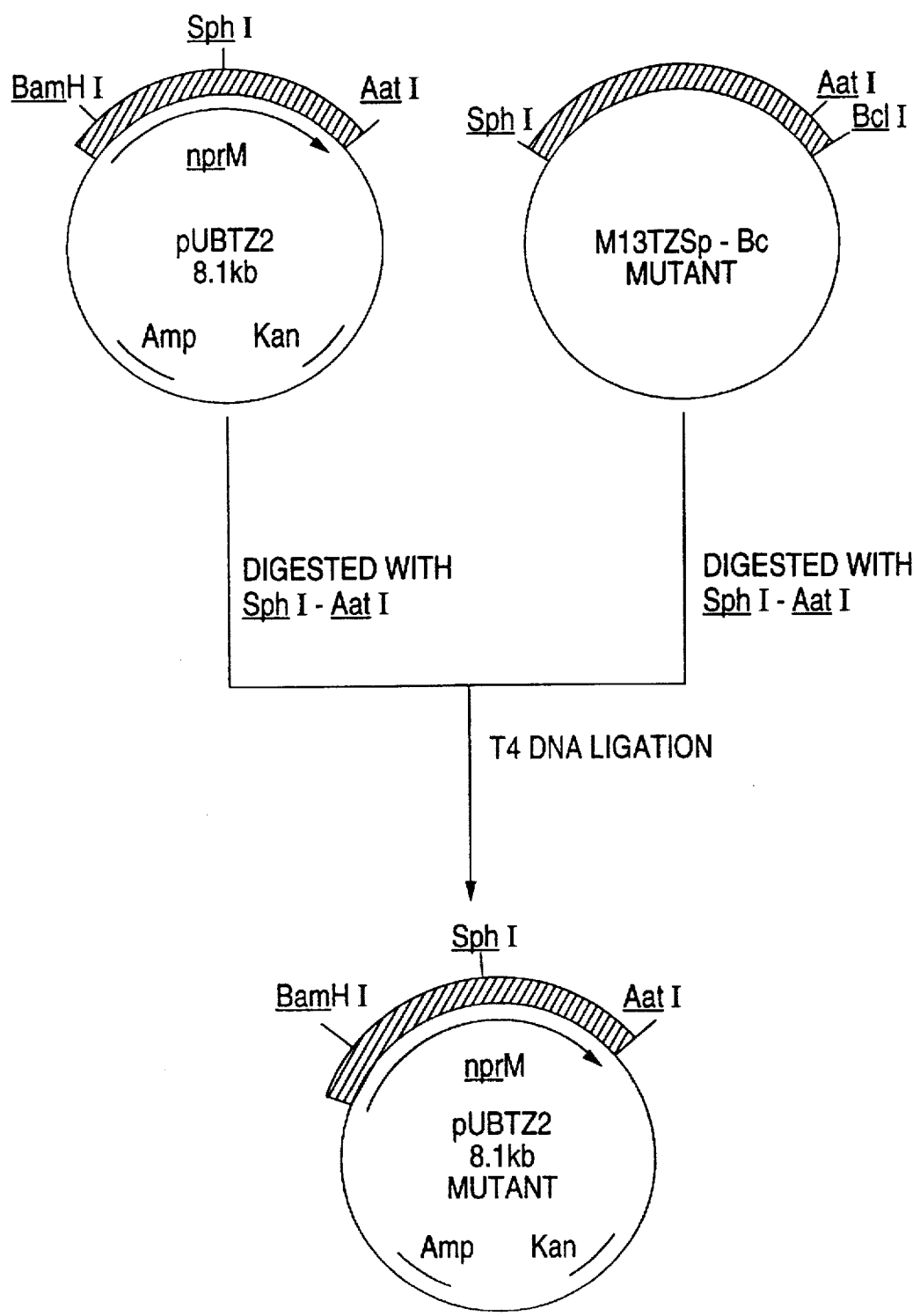
FIG. 8 shows the scheme used for constructing a recombinant plasmid pUBTZ2(N227H mutant) from the plasmid pUBTZ2 and M13TZSp-Bc(N227H mutant).

The plasmid pUBTZ2 was digested with restriction enzyme SphI and AatI, and a 7.6 kb fragment was isolated. The mutated SphI-AatI fragment of the nprM gene (about 550 bp) was ligated with the thus obtained pUBTZ2 SphI- AatI fragment using a Takara Shuzo DNA ligation kit. The ligation mixture was used to transform *Escherichia coli* JM103 in a conventional manner to give recombinant plasmid pUBTZ2 (N227H) (FIG. 8).

b) Site 150 Trp mutagenesis and preparation of the mutant enzyme (D150W-N227H)

The plasmid pUBTZ2 (N227H) was used as a template for polymerase chain reaction. The mutagenesis primer of SEQ ID NO:2, and the reverse-direction primer of SEQ ID NO:3 were used.

1 ng of plasmid pUBTZ2 (N227H) was dissolved in 100 µl of the reaction mixture of PCR (67 mM Tris-hydrochloride at pH 8.8, 16.6 mM ammonium sulfate, 6.7 mM MgCl2, 10 mM 2-mercaptoethanol, 0.05 mM dATP, 0.05 mM dTTP, 0.05 mM dGTP, 0.05 mM dCTP, 1 µM mutagenesis primer, 1 µM reverse-direction primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA (D150W-N227H).

20 µl of a reaction mixture (50 mM Tris-hydrochloride at pH 7.5, 10 mM MgCl2, 100 mM NaCl, 1 mM DTT) containing half the amount of the amplified DNA was digested with 5 units each of restriction enzyme SphI and AatI at 37° C. for 2 hours, and was incubated at 70° C. for 5 minutes. The mutated SphI-AatI fragment was ligated with the 7.6 kb SphI-AatI fragment of pUBTZ2 using a Takara Shuzo DNA ligation kit. The ligation mixture was used to transform *Escherichia coli* JM103 in a conventional method to give a transformant JM103/pUBTZ2 (D150W-N227H). The substituted amino acid was confirmed by the determination of the nucleotide sequence of this plasmid.

The plasmid DNA was used for transformation of *Bacillus subtilis* MT-2 and the modified protease (D150W-N227H) was prepared by the same method as described in example 1.

Figure 9:
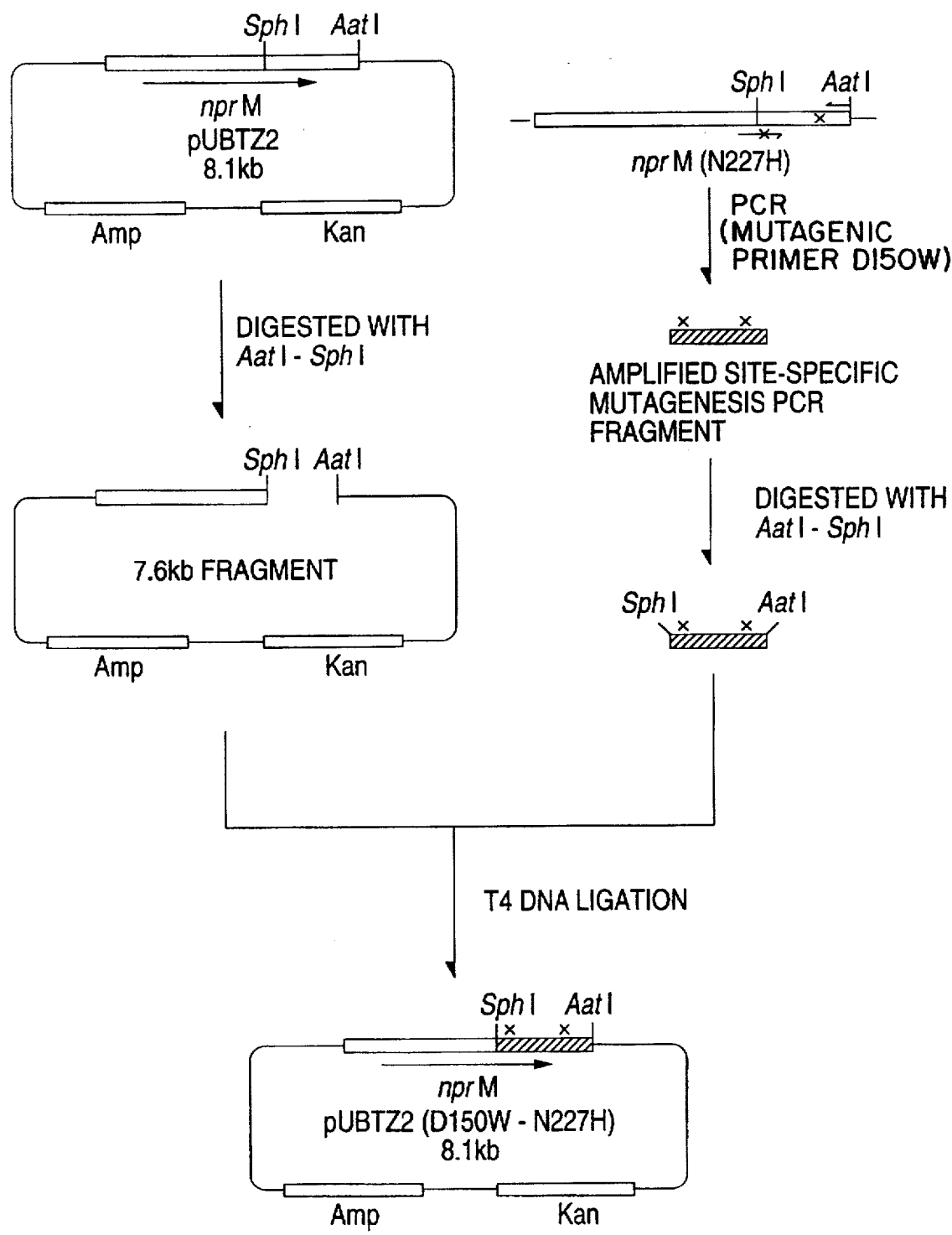
FIG. 9 shows the scheme used for constructing a recombinant plasmid named pUBTZ2(D150W-N227H) from the plasmid pUBTZ2 and the mutant DNA fragment obtained by polymerase chain reactin

FIG. 9 shows the scheme used for constructing recombinant plasmid pUBTZ2 (D150W-N227H).

EXAMPLE 3

[Synthesis of the Modified Protease which has the Triple Replacements at the 144th Amino Acid Residue from Leucine to to Serine, the 150th Amino Acid Residue from Aspartic Acid to Tryptophan and the 227th Amino Acid Residue from Asparagine to Histidine (L144S-D150W-N227H)]

A three-site mutant of thermolysin-like neutral metalloprotease was constructed as follows.

a) Site 144 Ser mutagenesis

The mutagenic oligonucleotide used for the replacement of the 144th residue (leucine to serine) is shown below.

(SEQ ID NO:5)

5'-TACCGCATGCGTTGACTCATGTGCGAC-3'

SphI    Ser

Furthermore, a sense primer was synthesized having the nucleotide sequence described below.

(SEQ ID NO:6)

5'-CCGAATTTGGACACGAAAGGATCC-3'

BamHI 1 ng of the plasmid pUBTZ2 was dissolved in 100 µl of the reaction mixture for PCR (67 mM Tris-hydrochloride at pH 8.8, 16.6 mM ammonium sulfate, 6.7 mM MgCl2, 10 mM 2-mercaptoethanol, 0.05 mM dATP, 0.05 mM dTTp, 0.05 mM dGTP, 0.05 mM dCTP, 1 µM mutagenesis primer, 1 µM sense primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA.

20 µl of a reaction mixture (50 mM Tris-hydrochloride at pH 7.5, 10 mM MgCl2, 0.1M NaCl, 1 mM DTT) containing half the amount of the amplified DNA was digested with 5 units each of restriction enzyme BamI and SphI at 37° C. for 2 hours, and was incubated at 70° C. for 5 minutes. The mutated BamI-SphI fragment was ligated with the BamI-SphI fragment of pUBTZ2 (7.4 kb) using a Takara Shuzo DNA ligation kit. The ligation mixture was used to transform *Escherichia coli* JM103 in a conventional method to give a transformant JM103/pUBTZ2 (L144S). The substituted amino acid was confirmed by the determination of the nucleotide sequence of this plasmid.

Figure 10:
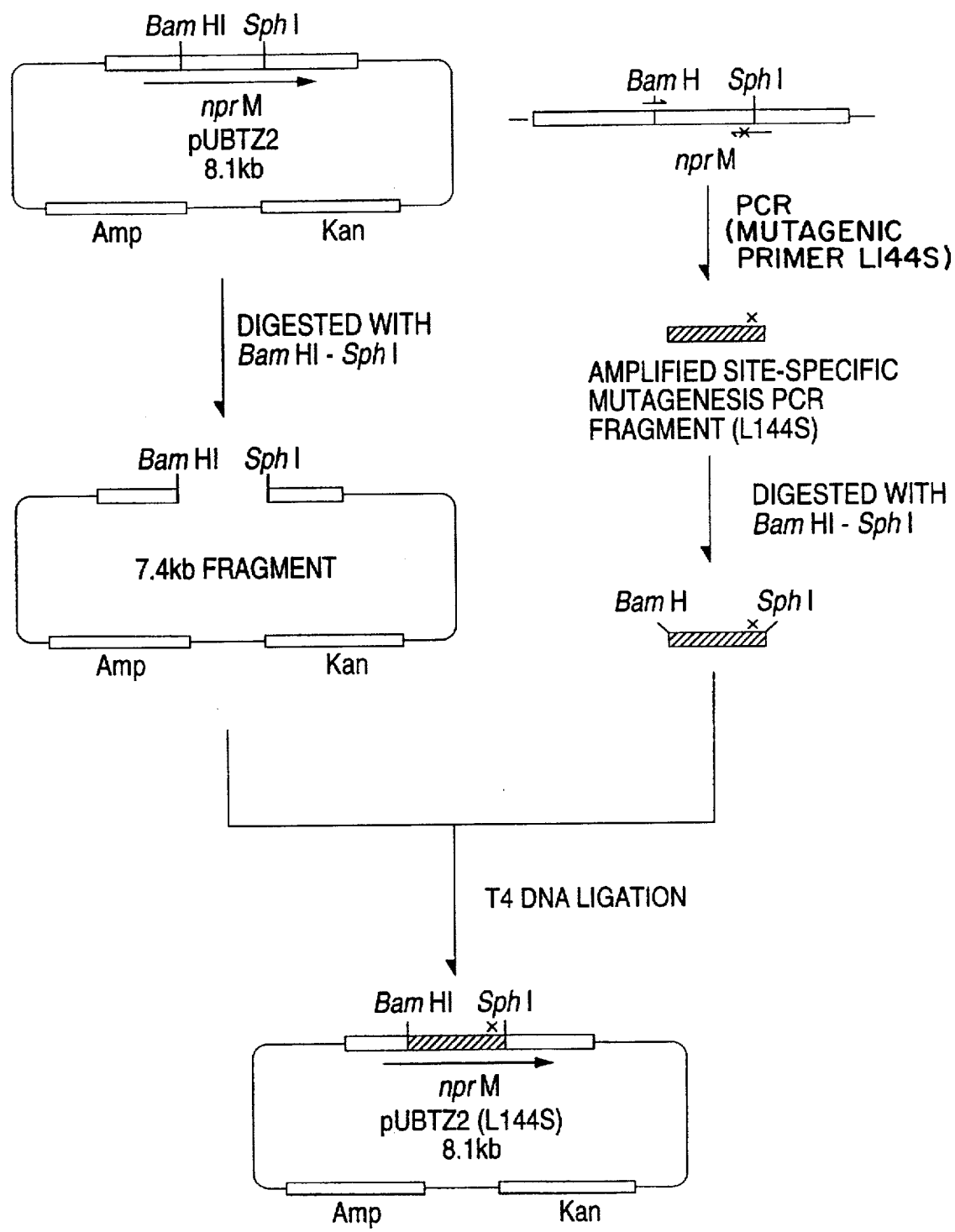
FIG. 10 shows the scheme used for constructing a recombinant plasmid named pUBTZ2(L144S) from the plasmid pUBTZ2 and the mutant DNA fragment obtained by polymerase chain reaction.

FIG. 10 shows the scheme used for constructing recombinant plasmid pUBTZ2(L144S).

b) Construction of the plasmid pUBTZ2(L144S-D150W-N227H)

20 µl of a reaction mixture (50 mM Tris-hydrochloride at pH 7.5, 10 mM MgCl2, 0.1M NaCl, 1 mM DTT) containing 1 µg pUBTZ2(D150W-N227H) obtained in Example 2 was digested with 5 units of each restriction enzyme SphI and AatI at 37° C. for 2 hours, and was incubated at 70° C. for 5 minutes. The mutated SphI-AatI fragment was ligated with the 7.6 kb SphI-AatI fragment of pUBTZ2 (L144S) using a Takara Shuzo DNA ligation kit. The ligation mixture was used to transform *Escherichia coli* JM103 in a conventional method to give a transformant JM103/pUBTZ2 (L144S-D150W-N227H). The substituted amino acid was confirmed by the determination of the nucleotide sequence of this plasmid.

The plasmid DNA was used for transformation of *Bacillus subtilis* MT-2 and the modified protease (L144S-D150W-N227H) was prepared by the same method as described in example 1.

Figure 11:
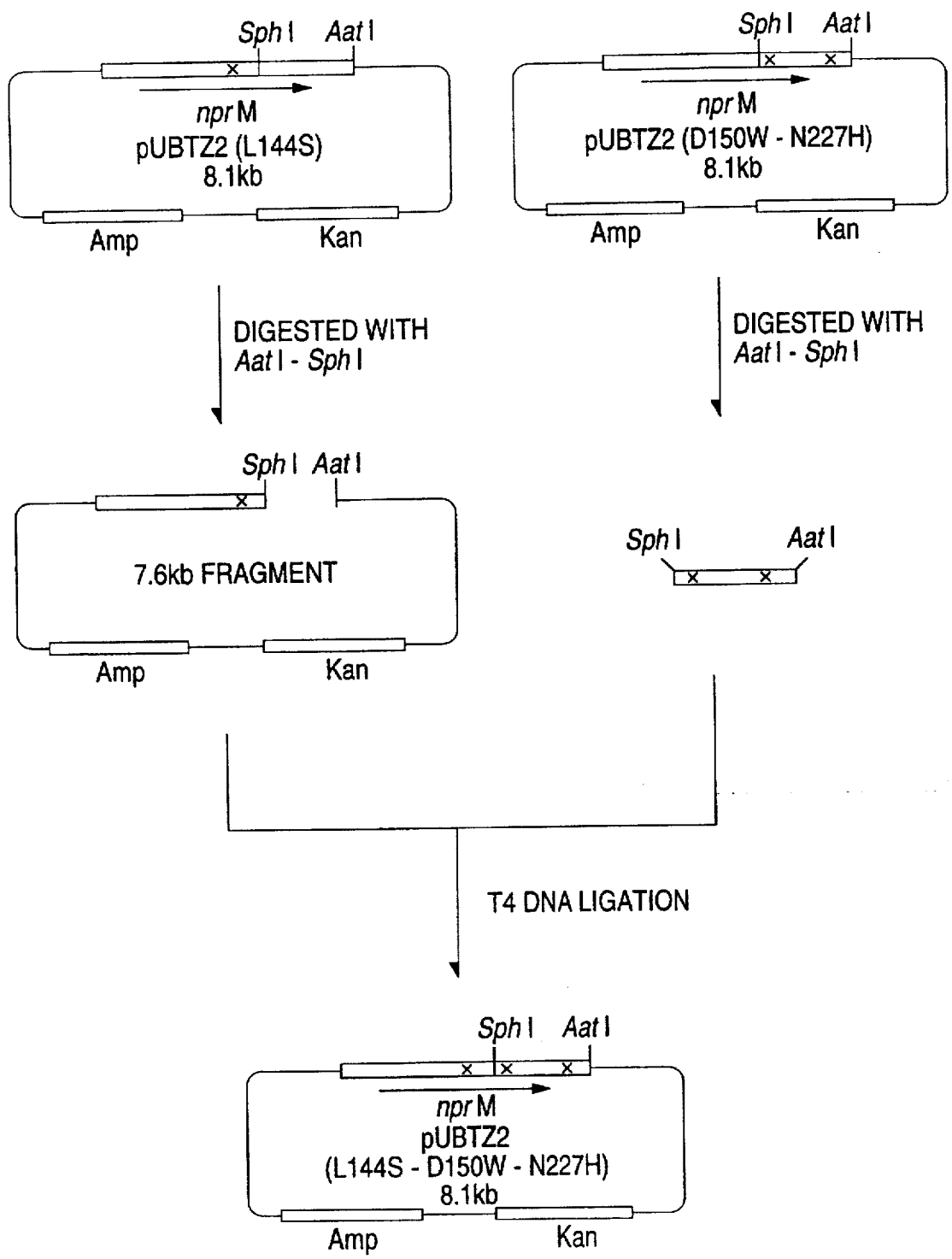
FIG. 11 shows the scheme used for constructing a recombinant plasmid named pUBTZ2(144S-D150W-N227H) from the plasmid pUBTZ2(L144S) and the plasmid pUBTZ2(D150W-N227).

FIG. 11 shows the scheme used for constructing recombinant plasmid pUBTZ2(L144S-D150W-N227H).

EXAMPLE 4

[Determination of the Activity of the Modified Proteases]

(1) Z-APM synthetic activity

Z-APM synthetic activity was determined by high pressure liquid chromatography (HPLC) after condensation reaction of benzyloxycarbonyl-L-aspartic acid (Z-Asp) and L-phenylalanine methyl ester hydrochloride (L-PM). The mutant proteases were incubated with 0.1M Z-Asp and 0.1M L-PM in 0.1M Tris-maleate buffer (pH 6 or 7) at 35° C. for 30 minutes. The reaction was terminated by addition of equal volume of 0.125M EDTA. The amount of synthesized Z-APM was determined by HPLC equipped with a cosmosil C-18 column (Nacalai tesque). The HPLC was carried out with 60 mM Triehylamine-phosphate buffer (pH 3.0) containing 40% acetonitrile as eluent at a flow rate of 1.0 ml/min. and eluted Z-APM was determined by absorbance at 224 nm. The activity of synthesizing 1 mole Z-APM in a second is defined as 1 katal (kat).

For comparison purposes applicant also synthesized and examined all other D150 mutants using a random mutagenesis primer.

The nucleotide sequence of the random mutagenesis primer was (SEQ ID NO:7)

5'-AACGCATGCGGTAACCXXXTATACAGC-3'

SphI        Codon of the 150th amino acid wherein each X stands for G, A, T or C independently.

This primer has the variation at the codon of 150th amino acid residue and can introduce all 20 amino acid residues at the 150th position. We have introduced various mutations at the 150th position by using this mutagenesis primer and studied all except tryptophan.

1 ng of plasmid pUBTZ2 was dissolved in 100 μl of the reaction mixture of PCR (67 mM Tris-hydrochloride at pH 8.8, 16.6 mM ammonium sulfate, 6.7 mM MgCl2, 10 mM 2-mercaptoethanol, 0.05 mM dATP, 0.05 mM dTTp, 0.05 mM dGTP, 0.05 mM dCTP, 1 μM mutagenesis primer, 1 μM reverse-direction primer), and 1 unit of Tth DNA polymerase was added. The solution was covered with one drop of mineral oil. The denaturation at 93° C. for 1 minute, the annealing at 45° C. for 1 minute and the extension at 72° C. for 45 seconds were repeated 30 times. After the reaction, the water layer was recovered, extracted with phenol and treated with ethanol to recover the amplified DNA.

20 μl of a reaction mixture (50 mM Tris-hydrochloride at pH 7.5, 10 mM MgCl2, 0.1M NaCl, 1 mM DTT) containing half the amount of the amplified DNA was digested with 5 units of each SphI and AatI at 37° C. for 2 hours, and was incubated at 70° C. for 5 minutes. The mutated SphI-AatI fragment was ligated with the 7.6 kb SphI-AatI fragment of pUBTZ2 using a Takara Shuzo DNA ligation kit. The ligation mixture was used to transform *Escherichia coli* JM103 in a conventional method to give a transformant JM103/pUBTZ2. The substituted amino acid was confirmed by the determination of the nucleotide sequence of the plasmid.

Plasmid DNA except D150W mutant was isolated by the rapid alkaline-SDS method. Transformation to *Bacillus subtilis* MT-2 strain was done by the competent cell method.

A single colony of each different *Bacillus subtilis* MT-2/pUBTZ2 (mutant) transformant was inoculated in 5 ml of LB medium containing kanamycin (5 μg/ml) and incubated at 37° C. overnight. The culture was transferred to 500 ml of 2 L medium (2% Bacto tryptone, 1% yeast extract, 0.5% NaCl) containing kanamycin (5 μg/ml) and incubated at 37° C. for 20 hours. The culture broth was centrifuged at 8,000 rpm for 30 minutes to remove bacteria, ammonium sulfate was added to the supernatant to attain 60% saturation and the mixture was stirred overnight at 4° C.

The precipitate was recovered by centrifugation and dissolved in 10 ml of Buffer A (20 mM Tris-hydrochloride at pH 9.0, 10 mM CaCl2). The enzyme solution was applied to 20 ml of Butyl-Toyopearl, followed by elution with Buffer A at a flow rate of 1.5 ml/minute. Active fractions were combined and subjected to salting out with 60% saturated ammonium sulfate. The precipitate was collected by centrifugation at 15,000 rpm. for 30 minutes, and dissolved in 5 ml of Buffer B (20 mM Tris-hydrochloride at pH 7.5, 10 mM CaCl2). The enzyme solution was further applied to a gel-filtration column (TSK Gel G2000 SW (21.5×300 mm)), followed by elution with Buffer B at a flow rate of 1 ml/minute. Active fractions were combined to give each purified enzymes.

Figure 12:
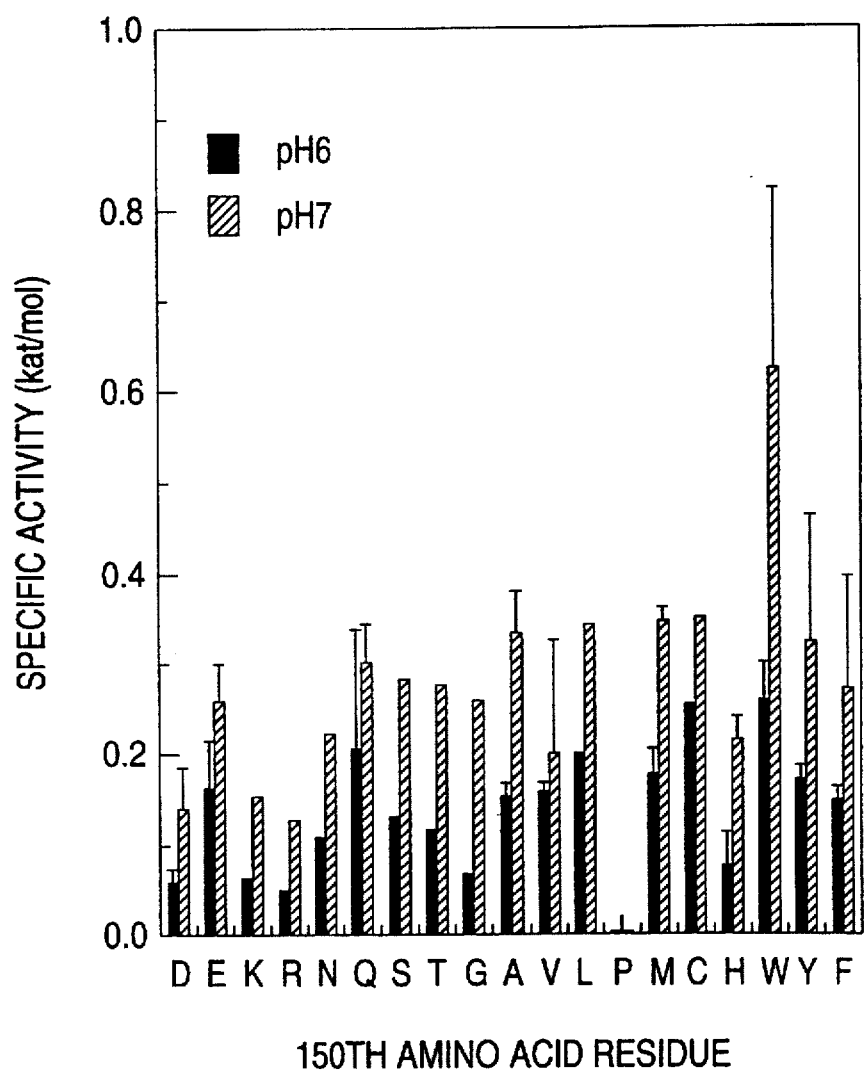
FIG. 12 shows Z-APM synthetic activities of modified enzymes. Abbreviations are indicating one letter code for amino acids. "D" in 150th amino acid residue means wild type thermolysin-like neutral metallo-protease. Enzyme activity which synthesizes 1 mole of Z-APM in a second is defined as 1 katal (kat).

The synthetic activities of the modified proteases in which the 150th aspartic acid residue is replaced by other amino acid residues (D150W mutants) are shown in FIG. 12. The mutant having the 150th aspartic acid residue replaced to tryptophan (D150W) shows markedly high specific activity i.e. about 4 times higher than wild type thermolysin (D), while most of the other mutants show higher activities than wild type thermolysin (D), but these activities are much lower than of D150W. The tryptophan mutant is clearly the highest in activity.

The activity as determined for additional two multiple-site mutants, namely the 2-site mutant D150W-N227H (i.e. 150th aspartic acid to tryptophan and 227th asparagine to histidine), and the 3-site mutant L144S-D150W-N227H (i.e. 144th leucine to serine, 150th aspartic acid to tryptophan and 227th asparagine to histidine) is even higher, as is shown in Table 1.

(2) Z-APM hydrolytic activity

Hydrolysis of Z-APM into Z-Asp and PM by the modified proteases was measured by following the decrease in absorbance at 224 nm according to the method of Inoue (Inoue, K., (1992) J. Biochem., 112, 335–340). Three ml of 1 mM Z-APM dissolved in 0.1M Tris-hydrochloride buffer (pH 7.0) was incubated with modified proteases at 35° C. and decrease of absorbance at 224 nm was monitored. The amount of hydrolyzed Z-APM was determined by the molar absorptivity difference Δε224 calculated to be −493 (M−1·cm−1).

Figure 13:
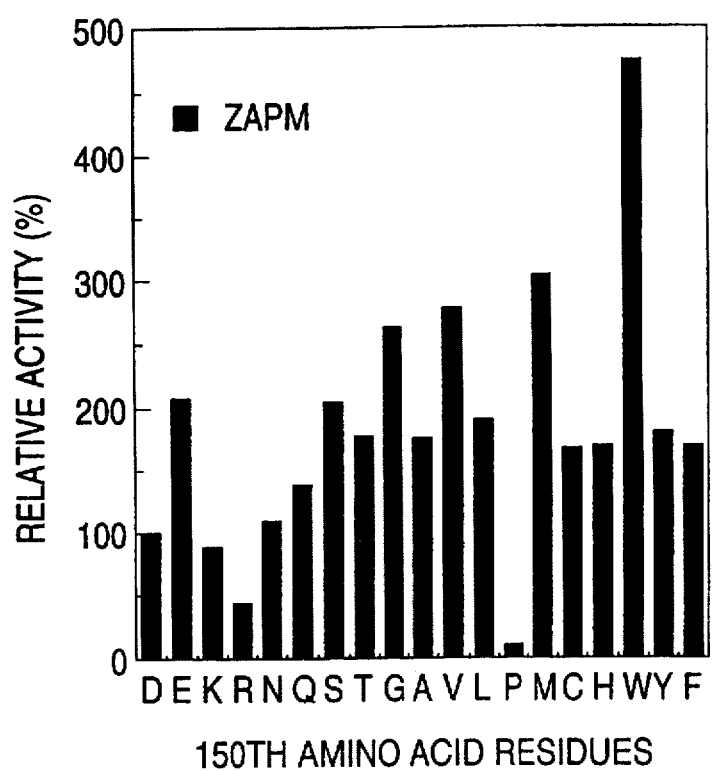
FIG. 13 shows hydrolytic activities of modified enzymes for Z-APM.20

The activities of D150 mutants are shown in FIG. 13. D150W mutant shows markedly high activity which is about 4 times higher than that of wild type thermolysin. Most of the others show only about 1–3 times higher specific activities of Z-APM hydrolysis than wild type thermolysin(D). The tryptophan mutant is clearly much higher in activity.

The activity of D150W-N227H and L144S-D150W-N227H is also shown in Table 1. Their activities towards Z-APM hydrolysis are 6–7 times and 9–10 times higher than wild type, respectively.

TABLE 1

Summary of the activity of the modified proteases towards Z-APM synthesis and Z-APM hydrolysis

| | Activity for Z-APM | | |
|---|---|---|---|
| | Synthetic (kat/mole) | | Hydrolytic (kat/mole) |
| Enzymes | pH6 | pH7 | pH7.0 |
| Wild Type | 0.063 | 0.137 | 3.5 |
| D150W | 0.261 | 0.623 | 11.9 |
| D150W/N227H | 0.447 | 1.007 | 22.6 |
| L144S/D150W/N227H | 0.609 | 1.220 | 37.0 |

*: One katal (kat) is defined as the activity of synthesising or hydrolysing one mole Z-APM per second.

We claim:

1. A modified protease of thermolysin-like neutral metallo-protease having the amino acid sequence of SEQ ID NO:1, wherein the 150th aspartic acid residue is replaced with tryptophan.

2. A modified protease of thermolysin-like neutral metallo-protease according to claim 1, wherein the 227th asparagine residue is replaced with histidine.

3. A modified protease of thermolysin-like neutral metallo-protease according to claim 1, wherein the 144th leucine residue is replaced with serine.

4. A process for synthesizing benzyloxycarbonyl-α-L-aspartyl-L-phenylalanine methyl ester which comprises contacting the modified protease of claim 1 with a substrate solution containing benzyloxycarbonyl-α-L-aspartic acid and L- or D,L-phenylalanine methyl ester.

5. A process for digesting benzyloxycarbonyl-α-L-aspartyl-L-phenylalanine methyl ester which comprises contacting the modified protease of claim 1 with a substrate solution containing benzyloxycarbonyl-α-L-aspartyl-L-phenylalanine methyl ester.

6. A modified protease of thermolysin-like neutral metallo-protease according to claim 2, wherein the 144th leucine residue is replaced with serine.

* * * * *